United States Patent [19]

Moyer, Jr. et al.

[11] 4,191,701

[45] Mar. 4, 1980

[54] ALCOHOL SEPARATION

[75] Inventors: Charles E. Moyer, Jr., Charleston; George E. Keller, II, South Charleston; Robert W. Beisner; Wellington E. Walker, both of Charleston, all of W. Va.

[73] Assignee: Union Carbide Corporation, New York, N.Y.

[21] Appl. No.: 786,584

[22] Filed: Apr. 11, 1977

Related U.S. Application Data

[63] Continuation of Ser. No. 674,822, Apr. 8, 1976, abandoned, which is a continuation of Ser. No. 506,862, Sep. 17, 1974, abandoned.

[51] Int. Cl.$^2$ .................... C07C 27/06; C07C 27/34
[52] U.S. Cl. .................... 260/450; 260/449 L; 260/449.5
[58] Field of Search ............. 260/450, 449 R, 449 L, 260/449.5, 637; 203/49

[56] References Cited

U.S. PATENT DOCUMENTS

| | | | |
|---|---|---|---|
| 1,996,852 | 4/1935 | Bergell | 203/49 X |
| 3,409,515 | 11/1968 | Baird et al. | 203/49 |
| 3,833,634 | 9/1974 | Pruett et al. | 260/449 R |
| 3,857,902 | 12/1974 | Inomata et al. | 203/49 |

*Primary Examiner*—Howard T. Mars
*Attorney, Agent, or Firm*—Marylin Klosty

[57] ABSTRACT

The process involves the separation of product from a liquid homogeneous mixture obtained from the reaction of oxides of carbon (e.g. CO) and $H_2$ in a solvent solution containing a rhodium carbonyl complex catalyst. The solution stability of the catalyst is enhanced by volatilizing the product from the mixture while simultaneously maintaining the mixture in contact with CO gas.

4 Claims, No Drawings

ALCOHOL SEPARATION

This is a continuation of our prior U.S. applications Ser. No. 674,822 filed Apr. 8, 1976 now abandoned which is a continuation of application Ser. No. 506,862 filed Sept. 17, 1974, now abandoned.

This invention is concerned with the recovery of product from a homogeneous mixture containing a rhodium carbonyl complex catalyst. More particularly, this invention relates to the separation of the alcohol products of the reaction between oxides of carbon and hydrogen in a homogeneous liquid-phase containing a rhodium carbonyl complex.

There are described in Belgium Pat. No. 793,086, published June 20, 1973 and copending application Ser. No. 462,109, filed Apr. 18, 1974 now U.S. Pat. No. 3,957,857 issued May 18, 1976, processes involving the high pressure reaction of oxides of carbon and hydrogen in the presence of a rhodium carbonyl complex catalyst. It has been pointed out in Ser. No. 462,109 that a preferred rhodium carbonyl complex catalyst is a rhodium carbonyl cluster. The nature of that catalyst under the conditions of the reaction or as it is provided to the reaction can be characterized by its infrared spectrum. However, such catalysts frequently take another structure at temperatures and pressures lower than those used in the reaction.

In a preferred embodiment of those processes, the reaction is conducted as a homogeneous liquid phase which means that the catalyst and the alcohol products formed from the reaction are in a solution. The solution typically requires the presence of a solvent mainly to keep the catalyst in solution before and after the reaction. Since the main and the most valuable products of those processes are high boiling alkane polyols such as ethylene glycol, glycerine and 1,2-propylene glycol, and the secondary, and less valuable products are alkanols such as methanol, ethanol, etc., rather severe changes are required from the conditions of the reaction to those employed in the separation of product. And, since the most desired process is a continuous one, it is necessary to be able to recycle the catalyst to the reaction after the product has been removed.

However, rhodium carbonyl complexes vary in structure based e.g., upon the temperature, solvent, ligand, counter ion, and carbon monoxide and hydrogen pressure employed, such that a complex which may be extremely stable in a solution at one temperature could precipitate out of the solution at another temperature. In the case of large scale processes, catalyst losses are not usually tolerated. In the case of the processes of the copending applications, rhodium losses in the order of, e.g., about 0.1% by weight on a per pass basis would be sufficient to make the process uneconomical. On the open market, rhodium metal is priced in the neighborhood of about 715 U.S. dollars per troy ounce. Thus, the commercialization of these processes requires avoidance of a loss of an amount of rhodium metal which causes the cost of the products produced to be greater than that of the same products produced by other competitive processes.

There is described herein a process for the recovery of the alcohol products produced by these rhodium catalyzed reactions which reduces catalyst instability during that phase of a continuous process. By the terms "instability" and "unstable", when referring to the catalyst, it is meant that it is reduced to a condition where it becomes, or is, insoluble in the solution from which the product is being recovered.

The process of this invention involves the separation of product from a liquid homogeneous mixture obtained from the reaction of oxides of carbon and hydrogen in a solvent solution containing a rhodium carbonyl complex catalyst in a manner which minimizes catalyst instability. This is accomplished by the simple expedient of contacting the mixture with carbon monoxide gas while simultaneously volatilizing product from the mixture. The term "contacting", as used above, means a physical touching of the mixture and carbon monoxide gas as illustrated by providing the gas at the surface of the mixture, or bubbling the gas through the mixture, and the like.

The typical solution (i.e., liquid homogeneous mixture) which is to be treated in accordance with this invention will contain the products of the reaction, such as ethylene glycol, glycerine, propylene glycol, methanol, ethanol, propanol, ethylene glycol monoformate, methyl formate, ethyl formate, and the like, the catalyst in the form of a rhodium carbonyl complex and a solvent for the catalyst which is mutually compatible with the products of the reaction. The amount of product in the solution can vary greatly, from about 1 to about 75 weight percent of the solution. The solvent can be present in a broad range, such as from about 25 to about 99 weight percent of the solution. The catalyst concentration can vary greatly, from about $1 \times 10^{-6}$ weight percent, or even less, to about 30 weight percent, based on its rhodium metal content. However, the composition of the liquid homogeneous mixture being treated according to this invention is not narrowly critical. All that is required is any amount of reaction product to be recovered, and any amount of a rhodium carbonyl complex solvated by a solvent.

The rhodium carbonyl complex present in the solution does not have to have the structure of the rhodium carbonyl complex which catalyzed the reaction between the CO and $H_2$. In those cases where the rhodium carbonyl complex acting as the catalyst has the formula $[Rh_{12}(CO)_{30}]^{2-}$ and the structure as shown in U.S. Pat. No. 3,957,857, the rhodium carbonyl complex which exists in the homogeneous mixture may be an anion of the formula $Rh_6(CO)_{16}$ of the structure as shown in said U.S. Pat. No. 3,957,857, or it may be the anion of lower rhodium containing compounds, from monorhodium carbonyl and up. All that is required for the process of this invention is that the rhodium compound contain —CO bonded to rhodium and be in solution.

The solubilization of the rhodium carbonyl complex is typically dependent upon the solvent used to effect the homogeneous mixture. The desired solvent is any liquid material which dissolves or keeps in solution the components of the homogeneous mixture taken from the reactor. It must be solution compatible with the reaction products and the rhodium carbonyl complex.

Illustrative solvents which are generally suitable in making the homogeneous mixture, include, for example, saturated and aromatic hydrocarbons, e.g., hexane, octane, dodecane, naphtha, decalin, tetrahydronaphthalene, kerosene, mineral oil, cyclohexane, cycloheptane, alkylcycloalkane, benzene, toluene, xylene, naphthalen, alkylnaphthalene, etc.; ethers such as tetrahydrofuran, tetrahydropyran, diethyl ether, 1,2-dimethoxybenzene, 1,2-ethoxybenzene, the mono- and dialkyl ethers of ethylene glycol, of propylene glycol, of butylene glycol, of diethylene glycol, of dipropylene glycol, of triethylene glycol, of tetraethylene glycol, of dibutylene glycol, of oxyethyleneoxypropylene glycol etc.; carboxylic acids such as acetic acid, propionic acid, butyric acid, caproic acid, stearic acid, benzoic acid, cyclohexanecarboxylic acid, etc.; alkanols such as methanol, ethanol, propanol, isobutanol, 2-ethylhexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; water; anhydrides such as phthalic anhydride, acetic anhydride etc.; gamma-butyrolactone, delta-valerolactone, and others. Tetrahydrofuran, dioxane, and the mono and dialkyl ethers of triethylene and tetraethylene glycol, gamma-butyrolactone and delta-valerolactone are generally preferred solvents.

Because the rhodium carbonyl complexes are typically ionic, they can be associated with a counter-ion. The counter-ion may be rhodium per se, hydrogen, ammonia, any monovalent or polyvalent metal, and a broad range of organic compounds, such as those characterized hereinafter as ligands.

The monovalent or polyvalent metal counter-ion may include lithium, sodium, potassium, rubidium, cesium, francium, beryllium, magnesium, calcium, strontium, barium, radium, scandium, yttrium, the rare earth metals (especially, e.g., cerium, praseodymium, and europium), titanium, zirconium, hafnium, manganese, rhenium, iron, ruthenium, osmium, cobalt, rhodium, iridium, nickel, palladium, platinum, copper, silver, gold, boron, aluminum, gallium, indium and thallium.

The organic counter-ions may result from "complexing" organic compounds with the rhodium carbonyl ions or by ionically associating with them.

The term "complex" means a coordination compound formed by the union of one or more electronically rich molecules or atoms capable of independent existence with one or more electronically poor molecules or atoms, each of which is also capable of independent existence. The rhodium carbonyl complexes may be associations of organic ligands with rhodium carbonyl solutions. The complex may also be formed from the reaction of CO and $H_2$ with the rhodium carbonyl solution.

Organic ligands which are suitable in the practice of the invention contain at least one nitrogen atom (hereinafter called Lewis base nitrogen atom) and/or at least one oxygen atom (hereafter called Lewis base oxygen atom), said atoms possessing a pair of electrons available for the formation of coordinate bonds with rhodium. Desirably, the organic ligand contains at least two Lewis base nitrogen atoms, or at least two Lewis base oxygen atoms, or at least one Lewis base nitrogen atom plus at least one Lewis base oxygen atom, said atoms possessing a pair of electrons available for the formations of coordinate bonds with rhodium, and said organic ligand forming with rhodium per se a chelate structure. In suitable embodiments the organic ligands contain from 2 and upwards to 4 Lewis base atoms, preferably from 2 to 3 such atoms, and more preferably 2 Lewis base atoms. These organic ligands are said to be multidentate or polydentate, that is to say, such ligands are bidentate, tridentate, or quadridentate, depending on whether 2, 3 or 4 Lewis base atoms are involved in the formations of complexed structures with rhodium.

Organic ligands which contain at least one Lewis base nitrogen atom will oftentimes hereinafter be referred to as "organic nitrogen ligands"; those ligands which contain at least one Lewis base oxygen atom will oftentimes be referred to as "organic oxygen ligands"; and those which contain at least one Lewis base nitrogen atom plus at least one Lewis base oxygen atom will oftentimes be referred to as "organic aza-oxa ligands".

Suitable organic nitrogen ligands most generally contain carbon, hydrogen, and nitrogen atoms. Suitable organic oxygen ligands most generally contain carbon, hydrogen, and oxygen atoms. Suitable organic aza-oxa ligands most generally contain carbon, hydrogen, oxygen, and nitrogen atoms. The carbon atoms can be acyclic and/or cyclic such as aliphatic, cycloaliphatic, aromatic (including fused and bridged) carbon atoms, and the like. Preferably, the organic ligands contain from 2 to 20 carbon atoms. The nitrogen atoms can be in the form of imino (—N=),

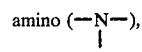

nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic),

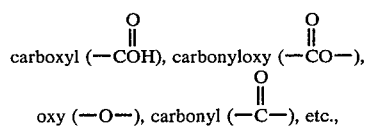

all of said groups containing Lewis base oxygen atoms. In this respect, it is the "hydroxyl" oxygen in the

and the "oxy" oxygen in the

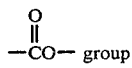

that are the Lewis base atoms. The organic ligands may also contain other atoms and/or groups such as alkyl, cycloalkyl, aryl, chloro, thiaalkyl, trialkylsilyl, and the like.

Illustrative organic nitrogen ligands include for instance, N,N,N',N',-tetramethylethylenediamine, N,N,N',N'-tetraethylethylenediamine, N,N,N',N'-tetrapropylethylenediamine, N,N,N',N'-tetramethylmethylenediamine, N,N,N',N'-tetraethylmethylenediamine, N,N,N',N'-tetraisobutylmethylenediamine, piperazine, N-methylpiperazine, N-ethylpiperazine, 2-methyl-N-methylpiperazine, 2,2'-dipyridyl, methyl-substituted 2,2'-dipyridyl, ethyl-substituted 2,2'-dipyridyl, 1,4-diazabicyclo[2.2.2]octane, methyl-substituted 1,4-diazabicyclo[2.2.2]octane, purine, 2-amino-pyridine, 2-(dimethylamine) pyridine, 1,10-phenanthroline, methyl-substituted 1,10-phenanthroline, 2-(dimethylamino)-6-methoxyquinoline, 7-chloro-1,10-phenanthroline, 4-triethylsilyl-2,2'-dipyridyl, 5-(thiapentyl)-1,10-phenanthroline, and the like.

Illustrative organic oxygen ligands include by way of illustrations, glycolic acid, methoxyacetic acid, ethoxyacetic acid, diglycolic acid, thiodiglycolic acid, diether ether, tetrahydrofuran, dioxane, tetrahydropyran, pyrocatechol, citric acid, 2-methoxy ethanol, 2-ethoxyethanol, 2-n-propoxyethanol, 2-n-butylethanol, 1,2,3-trihydroxybenzene, 1,2,4-trihydroxybenzene, 2,3-dihydroxynaphthalene, cyclohexane-1,2-diol, oxetane, 1,2-dimethoxybenzene, 1,2-diethoxybenzene, methyl acetate, ethanol, 1,2-dimethoxyethane, 1,2-diethoxyethane, 1,2-di-n-propoxyethane, 1,2-di-n-butoxyethane, pentane-2,4-dione, hexane-2,4-dione, heptane-3,5-dione, octane-2,4-dione, 1-phenylbutane-1,3-dione, 3-methylpentane-2,4-dione; the mono- and dialkyl ethers of propylene glycol, of diethylene glycol of dipropylene glycol; and the like.

Illustrative organic aza-oxa ligands include, for example, ethanolamine, diethanolamine, isopropanolamine, di-n-propanolamine, N,N-dimethylglycine, N,N-diethylglycine, iminodiacetic acid, N-methyliminodiacetic acid, N-methyldiethanolamine, 2-hydroxypyridine, methyl-substituted 2-hydroxypyridine, picolinic acid, methyl-substituted picolinic acid, nitrilotriacetic acid, 2,5-dicarboxypiperazine, N-(2-hydroxyethyl) iminodiacetic acid, ethylenediaminetetraacetic acid, 2,6-dicarboxypyridine, 8-hydroxyquinoline, 2-carboxyquinoline, cyclohexane-1,2-diamine-N,N,N',N'-tetraacetic acid, the tetramethyl ester of ethylenediaminetetraacetic acid, and the like.

Other organic counter-ions are formed by ionic association with the rhodium carbonyl cluster ions. They are from organic compounds which possess Lewis base nitrogen atoms and typically are composed of carbon, hydrogen and nitrogen. Illustrative of such compounds are, e.g., piperidine, 2-methylpiperidine, 3-methylpiperidine, pyridine, 2-methylpyridine, 4-ethylpiperidine, triethylamine, benzyltrimethyl ammonium acetate and formate, tri-n-butylamine, dibutylamine, methylamine, dodecylamine, morpholine, aniline, benzylamine, octadecylamine, naphthylamine, cyclohexylamine, and the like.

The manner of separating the reaction product(s) from the homogeneous mixture may include distillation and gas stripping. The separation may be effected at subatmospheric, atmospheric and superatmospheric pressure conditions and the temperature at which separation is effected is lower than that which causes the available CO to react with product, solvent and/or available hydrogen. The pressures used may range from about 0.001 to about 1000 atmospheres of pressure. The temperature may range from about 50° C. to about 300° C., more desirably from about 75° C. to about 250° C., and most desirably from about 100° C. to about 200° C.

This invention includes the presence of CO gas in contact with the homogeneous mixture during separation of reaction product. The carbon monoxide gas may be added to the atmosphere above a liquid body or film of the homogeneous mixture undergoing product separation by distillation (e.g., by conventional distillation or by thin-film evaporation). The amount of CO gas added to the atmosphere over the liquid body or film should be sufficient to reduce the amount of rhodium lost from the mixture when CO is not used. In the case of thin film evaporation, the CO gas can be supplied as impinging stream on the film so as to act as a stripping gas as well. In addition, or alternatively, the CO gas can be bubbled through the liquid body to increase the rate at which CO is dissolved therein. By increasing the amount of the CO gas and/or its stream velocity, the gas can be used to strip product from the mixture to increase the rate of recovery of the product over distillation alone or to maintain the rate of recovery at lower temperatures and/or higher pressures. The CO may be mixed with hydrogen gas without adversely affecting the stabilization of the rhodium containing catalyst.

EXAMPLE I

The procedure in this Example, the runs of which are characterized in Table I below, involves charging the solutions to be treated to a 100 ml. 3-necked reaction flask equipped with a water condenser, a thermometer and a rubber syringe cap for sampling. The condenser was connected to a manometer and vacuum pump and the pressure in the flask was adjusted with a nitrogen bleed into the flask when necessary. The flask was equipped with a gas delivery sparge to a nozzle, all of which open to the bottom of the flask so as to be covered by any solution which is added to the flask. The gases added were carbon monoxide or nitrogen, as indicated in Table I below, and they were fed at a rate sufficient to provide constant bubbling of the gases through the liquid in which the sparge was immersed. There was no effort to determine carbon monoxide and nitrogen sparge rates in these runs. The flask was immersed in a constant temperature bath set at 150° C. and the solution in the flask was sampled at intervals and analyzed by atomic absorption spectroscopy.

TABLE I

| Run No. | Inert Gas Sparge | Pressure | Cs Salt | Rh.Recovered ppm[a] (in parenthesis-% recovered) | | | | | |
|---|---|---|---|---|---|---|---|---|---|
| | | | | 0 min. | 10 min. | 20 min. | 30 min. | 60 min. | 90 min. |
| 1. | CO | Atmos. | Cs2HP[b] | 3840 | 3130 | 2850 | 2590 | | |
| 2. | CO | Atmos. | None | 3190 | 2675 | 2860 | 3020 | | |
| 3. | CO | 50 mm. | None | 3190 | 3880 | 4200 | 4100 | | |
| 4. | CO | 10 mm. | Cs2HP[b] | 3840 | 3530 | 3450 | 3380 (88.0) | | |
| 5. | CO | 10 mm. | None | 3100 | | | 2970 (95.8) | 2930 | 2620 (83.9) |
| 6. | $N_2$ | 10 mm. | None | 3110 | | | 1960 (63.0) | 1260 | 970 (31.2) |
| 7. | None, 140° | 10 mm. | None | 3280 | 3090 | 3010 | 2615 (79.7) | | |
| 8. | None, 160° | 10 mm. | None | 3280 | 2640 | 1550 | 1105 (33.6) | | |

[a]catalyst solutions tested as recovered from $H_2$/CO reaction runs under the following reaction conditions: Pressure: 6000 psig; 1/1 mole ratio of $H_2$/CO; Temperature: 220° C.; 4 hrs. reaction time; 100 ml. dimethylether of tetraethylene glycol (tetraglyme); 4.0mm Rh(CO)2AcAc*, 13 mm* distilled 2-hydroxypyridine, 0.67 mm* added Cs Salt if present as indicated.
[b]Cesium-2-hydroxypyridinate
*"AcAc" means acetylacetonate "mm" means millimoles

EXAMPLE II

In the runs set forth in Table II of this Example, the catalyst solution is added to a 100 ml. rocker bomb equipped with a glass liner. The bomb was flushed with the desired gas mixture, either carbon monoxide with or without hydrogen, or nitrogen and pressurized to the desired pressure as indicated in Table II. The bomb was thereafter slowly heated over a period of about two hours to the reaction temperature set forth in Table II and then vented to maintain the desired pressure in the bomb. The bomb was constantly rocked under the specified conditions for 24 hours, then cooled and the contents were analyzed for rhodium. In Table II below, the control runs used nitrogen rather than carbon monoxide and when a carbon monoxide run is indicated in Table II at less than 100% carbon monoxide the difference is made up by addition of hydrogen gas. The rhodium values expressed in Table II were those analyzed after the 24 hours period of each run.

It can be seen from Table II that when a higher pressure is employed, there is an overall average increase of 1032 parts per million (ppm) by weight of rhodium found over that obtained at atmospheric pressure. On the other hand, when the temperature is increased, there is an overall average loss of 2064 parts per million of weight of rhodium from that obtained at the lower temperature. There appears to be no difference shown, of any significance, in the results of the runs of Table II where 43% carbon monoxide is used instead of 100% carbon monoxide. The average difference was only an increase of 102 parts per million of weight favoring the higher carbon monoxide concentration.

The rhodium solution treated in Example II contained initially 2430 parts per million of rhodium, 526 parts per million of cesium, 5673 parts per million of 2-hydroxypyridine and the solvent was tetraglyme. All parts are by weight.

TABLE II

| Run No. | Pressure | Temp. °C. | % CO | Rh out, ppm* |
|---|---|---|---|---|
| 1 | 50 psig | 125 | 100 | 2431 |
| 2 | Atmospheric | 125 | 100 | 2405 |
| 3 | 50 psig | 175 | 100 | 2294 |
| 4 | Atmospheric | 175 | 100 | 1457 |
| 5 | 50 psig | 125 | 46 | 2399 |
| 6 | Atmospheric | 125 | 43 | 2333 |
| 7 | 50 psig | 175 | 43 | 1928 |
| 8 | Atmospheric | 175 | 43 | 1825 |
| Control | 25 | 150 | $N_2$(100%) | 2047 |
| Control | 25 | 150 | $N_2$(100%) | 2103 |

*Rhodium found in solution after run in parts by weight.

EXAMPLE III

The still used in this example was designed to operate continuously in order to more closely approximate commercial operation. The still included a kettle which was a 500 ml 3-necked flask, in which one neck contained a gas sparge tube, another neck contained a thermometer and the third neck contained a distillation column. At the top of the column was a distillation head equipped with a condenser and receiving flask for product recovery. The top of the condenser was connected to two Dry Ice$^{TM}$-acetone cooled traps located in series to collect any product which was not condensed due to entrainment of the sparge gas. In the side of the kettle was a withdrawal tube containing a stopcock used to remove the stripped rhodium solution continuously and to serve as a sample point for analysis. The distillation column was a 12" high Pyrex$^{TM}$ glass cylinder having a 1" inside diameter and a stopcock controlled feed tube approximately half-way up the column. Feeding was from a graduated flask to the distillation column. The interior of the distillation column was packed with standard stainless steel 312 protruded packing and the outside of the distillation column was wrapped with electrical wire which was used to control the temperature of the column through the application of an electrical current. In operating the equipment, the flask (kettle) temperature was maintained at 140° C. and the head temperature at the top of the column was 70° to 90° C. The overall temperature of the distillation column was maintained between 100°-130° C. for optimum refluxing. The solutions treated in this example were fed from the graduated flask through the feed tube, into the distillation column and finally into the kettle at a rate of 200 ml per hour. The initial solution charged contained 1.1 weight percent methanol, 5.1 weight percent ethylene glycol, 0.3 weight percent other products, 657 ppm by weight of solution of bistriphenylphosphine iminium ion, 620 ppm by weight of 4-phenylpyridine, 610 ppm of rhodium, and the remainder was tetraglyme.

In the first pass, carbon monoxide was fed at a rate of 10 liters per hour and the mean residence time in the still was 60 minutes. The rhodium loss determined by analysis after filling up the still and operating for one hour averaged 8 weight % per hour over five hours of operation. This is the equivalent of rhodium loss of 0.067 weight % for a 30 second residence time, a residence time which is more characteristic of commercial conditions. During this run, 0.6% of the feed was taken overhead and collected, demonstrating the sparge rate of CO was very low.

All of the liquid material was recombined from the overhead and the kettle, and re-introduced to the still. A second pass was effected using a carbon monoxide sparge rate of 20 liters per hour. The rhodium loss averaged 7% per hour providing essentially the same rhodium loss as indicated above for a 30 second residence time. This same procedure was repeated again for a third pass using nitrogen instead as the sparge gas and at a sparge rate of 20 liters per hour. In this last case, the rhodium loss averaged 38 weight % per hour over five hours continuous operation which would be equivalent to about 0.32 weight % loss for a 30 second residence time.

What is claimed is:

1. The process of separating products obtained from the reaction of an oxide of carbon and hydrogen in a solvent containing homogeneous liquid phase mixture containing a catalytic amount of rhodium in complex combination with carbon monoxide which comprises volatilizing said products of the reaction from the mixture at a temperature lower than that which causes the carbon monoxide to react with product, solvent or hydrogen, at a temperature which ranges from about 50° C. to about 300° C., and at a pressure which ranges from about 0.001 to about 1000 atmospheres while simultaneously maintaining the mixture in contact with added carbon monoxide gas.

2. The process of claim 1 wherein the carbon monoxide gas is provided at the surface of said mixture while volatilizing products therefrom.

3. The process of claim 1 wherein the carbon monoxide gas is bubbled through the mixture while volatilizing products therefrom.

4. The process of claim 1 wherein products volatilized from the liquid homogeneous mixture are alcohols selected from the group consisting of ethylene glycol, propylene glycol, glycerine, methanol and mixtures thereof.

* * * * *